(12) United States Patent
Guo et al.

(10) Patent No.: US 7,569,747 B2
(45) Date of Patent: Aug. 4, 2009

(54) BENTGRASS EVENT ASR-368 AND COMPOSITIONS AND METHODS FOR DETECTION THEREOF

(75) Inventors: Shirley Xiaoli Guo, Chesterfield, MO (US); Robert W. Harriman, Delaware, OH (US); Lisa Lee, Marysville, OH (US); Eric K. Nelson, Dublin, OH (US)

(73) Assignees: Monsanto Technology LLC, St. Louis, MO (US); The Scotts Company, Marysville, OH (US)

( * ) Notice: Subject to any disclaimer, the term of this patent is extended or adjusted under 35 U.S.C. 154(b) by 199 days.

(21) Appl. No.: 10/537,393

(22) PCT Filed: Dec. 3, 2003

(86) PCT No.: PCT/US03/38268

§ 371 (c)(1),
(2), (4) Date: Jul. 27, 2005

(87) PCT Pub. No.: WO2004/053062

PCT Pub. Date: Jun. 24, 2004

(65) Prior Publication Data

US 2006/0162007 A1    Jul. 20, 2006

Related U.S. Application Data

(60) Provisional application No. 60/431,153, filed on Dec. 5, 2002.

(51) Int. Cl.
*A01H 1/00* (2006.01)
*A01H 5/00* (2006.01)
*A01H 5/10* (2006.01)

(52) U.S. Cl. .............. 800/300; 800/266; 800/298; 800/320

(58) Field of Classification Search .................. None
See application file for complete search history.

(56) References Cited

U.S. PATENT DOCUMENTS 5,948,956 A    9/1999    Lee et al. ............ 800/320

FOREIGN PATENT DOCUMENTS

EP    1 167 531 A1    1/2002
WO    WO 99/19499    4/1999

OTHER PUBLICATIONS

Federal Register vol. 69, No. 2, pp. 315-317, Monday, Jan. 5, 2004.*
Hartman, Christina L., et al., Herbicide resistant turfgrass (*Agrostis palustris* Huds.) by biolistic transformation, *Bio/Technology* 12:919-923 (1994) (labeled XP-002444202).
Lee, Lisa, et al., "Development of Roundup Ready Creeping Bentgrass," 10th IAPTC&B Congress Posters, p. 79-A, No. P-1228 (2002) [abstract], BNSDOCID: <XP 008081741A_1_>; & *In Vitro Cellular & Developmental Biology—Animal*, vol. 38, No. Abstract, p. 79.A (Apr. 2002), XP-008081741; & *2002 Congress on In Vitro Biology*, Orlando, Florida, USA, Jun. 25-29, 2002, ISSN 1071-2690 [abstract].
Windels, P., et al., Development of a line specific GMO detection method: a case study, *Mededelingen van de Faculteit Landbouwwetenschappen Universiteit Gent*, Gent, BE 64(5b):459-462 (1999), ISSN 0368-9697 (labeled XP-001032975).

* cited by examiner

*Primary Examiner*—David H Kruse
(74) *Attorney, Agent, or Firm*—Pamela J. Sisson; Howrey LLP

(57) ABSTRACT

The present invention provides a bentgrass ASR-368 plant and seed. Also provided are assays for detecting the presence of the bentgrass ASR-368 based on a DNA sequence and the use of this DNA sequence as a molecular marker in a DNA detection method.

10 Claims, 5 Drawing Sheets

```
  1 aagcgagtat cctgATAAGA AAGGAAGAAG ACGATCGCTC TGTCTATGGG
 51 CGGGGCTCAG GGCGACGACA GAACCAGAGC TTTCGTCGTG AACAAAACAG
101 GGAAGGACCA AGCAGAGGA AGAGGAGAGG AAACAGAGAG AAAGAGGGGG
151 TTGGTAGGTA CTTGGTGGTC CCTGCTACTT CTCCAACAGC AGCAGAAAGG
201 AAAGAAGAAC GAACCAAGGC ACAAGTACGC TCCAACCGAG CCATCCCTTT
251 CTTCCCTTTA TCATTGACTT TAATCATGAG AAATCTAATT AATTAATTAA
301 ACTCTACGCA AAAGGCATAT AAAATTGTCA ATTATGCAAG GCAGTTGCCC
351 TGTTTCTGGT AGCCGGTTAC AACACAGGAA GACAACCAAA AGCGTCGGAA
401 AAGTGAGTTT AGTCGAATCT GAATTCAATG TGAAAGATTT TTGTAAAGAA
451 TGAAATAAAT CCCGATAAAA AAAGAATGAA CAAAAGGAAA CTAAAAAACT
501 GTGGATGTGA GTCCAACGTT TAAGCATATC GATGCAAACG TGATGAAGAA
551 CCAAACGCGC CGGCGGAAGA CGGATTCCCG GAAGACCAAA TTAAAGACGA
601 TAGTTGTCGA GCAAACGACC AAAAGAAGAA GATCCGACAT ATGCTTAAGA
651 AGAGAGTCGG GATAGTCCAA AATAAAACAA AGGTAAGATT ACCTGGTCAA
701 AAGTGAAAAC ATCAGTTAAA AGGTGGTATA AAGTAAAATA TCGGTAATAA
751 AAGGTGGCCC AAAGTGAAAT TTACTCTTTT CTACTATTAT AAAAATTGAG
801 GATGTTTTTG TCGGTACTTT GATACGTCAT TTTTGTATGA ATTGGTTTTT
851 AAGTTTATTC GCTTTTGGAA ATGCATATCT GTATTTGagt cgggtt
```

Figure 3

```
  1 agattgaatc ctGTTGCCGG TCTTGCGATG ATTATCATAT AATTTCTGTT
 51 GAATTACGTT AAGCATGTAA TAATTAACAT GTAATGCATG ACGTTATTTA
101 TGAGATGGGT TTTTATGATT AGAGTCCCGC AATTATACAT TTAATACGCG
151 ATAGAAAACA AAATATAGCG CGCAAACTAG GATAAATTAT CGCGCGCGGT
201 GTCATCTATG TTACTAGATC GGGGATATCC CCGGGGAATT CGGTACCATG
251 TACCACGGAA CAGAAAAAAG AAAGGCCCAC GGTTGTGCAG GAAACGGCCA
301 CCGCGCGAGC CAGCGCCTCA CGCCTCATCC GCCATTCCGT CGAGCACCCC
351 GCACGCGCCG CCGCTGCTAT GCTCCTCCGG CCGCGCCCCT TCCTCCTCCA
401 GGTCCTCACG CCGCTTCGCT CCTCCGCGC CCCCCTCGCG GTCCGCCGCA
451 CGCTCTCAGC gcacgccgcg gcag
```

Figure 4

5' GACATATGCTTAAGAAGAGAGTCG 3' (SEQ ID NO:1)
5' AATTCGGTACCATGTACCACGAAC 3' (SEQ ID NO:2)

Figure 5

BENTGRASS EVENT ASR-368 AND COMPOSITIONS AND METHODS FOR DETECTION THEREOF

This application is a §371 U.S. national phase application of International Application No. PCT/US2003/0038268 filed Dec. 3, 2003, and claims the benefit of priority to U.S. Provisional Application No. 60/431,153, filed Dec. 5, 2002.

FIELD OF THE INVENTION

The present invention relates to the field of plant molecular biology. More specifically, the invention relates to a glyphosate tolerant bentgrass plant event ASR-368 and to assays and methods for detecting the presence of bentgrass plant event ASR-368 DNA in a plant sample and compositions thereof.

BACKGROUND OF THE INVENTION

Bentgrass (*Agrostis stolonifera*) is an important turf species in many areas of the world. The methods of biotechnology have been applied to bentgrass for improvement of the agronomic traits. One such agronomic trait is herbicide tolerance, in particular, tolerance to glyphosate herbicide. The control of weeds in bentgrass is particularly problematic. Bentgrass used on golf greens is especially sensitive to many herbicides that are normally used on other turfgrasses or on other areas of a golf course. Annual grasses, such as, crabgrass, foxtail, dallisgrass, and goosegrass must be controlled by use of a variety of herbicides including bensulide, dithiopyr, oxadiazon, fenoxaprop and prodiamine applied at specific rates, environmental conditions, and seasons by expert applicators in order to be effective. Annual and perennial broadleaf weeds may be controlled in bentgrass turf by applications of herbicides that include 2,4-D, MCPP, dicamba, and mixtures of these. Many grass and broadleaf herbicides cannot be used on bentgrass golf greens because of injury to the bentgrass, or they are not registered for use on bentgrass. There is a need for a glyphosate tolerant bentgrass to replace the use of these herbicides and to provide a method for effective grass and broadleaf weed control in bentgrass turf when glyphosate herbicide is applied.

N-phosphonomethylglycine, also known as glyphosate, is a well-known herbicide that has activity on a broad spectrum of plant species. Glyphosate is the active ingredient of Roundup® (Monsanto Co.), a safe herbicide having a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants. Glyphosate tolerance can also be achieved by the expression of bacterial EPSPS variants and plant EPSPS variants that have lower affinity for glyphosate and therefore retain their catalytic activity in the presence of glyphosate (U.S. Pat. Nos. 5,633,435; 5,094,945, 4,535,060, and 6,040,497).

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of events in order to identify an event characterized by optimal expression of a introduced gene of interest. For example, it has been observed in plants and in other organisms that there may be a wide variation in levels of expression of an introduced transgene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual crossing using conventional breeding methods. Progeny of such crosses maintain the transgene expression characteristics of the original transformant. This strategy is used to ensure reliable gene expression in a number of varieties that are well adapted to local growing conditions and market demands.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Windels et al. (Med. Fac. Landbouww, Univ. Gent 64/5b:459-462, 1999), who identified glyphosate tolerant soybean event 40-3-2 by PCR using a primer set spanning the junction between the insert and flanking DNA, specifically one primer that included sequence from the insert and a second primer that included sequence from flanking DNA. Event-specific DNA detection methods for a glyphosate tolerant corn event have also been described (US 20020013960 A1, herein incorporated by reference in it's entirety).

The present invention relates to a glyphosate herbicide tolerant bentgrass plant ASR-368 and to DNA compositions that comprise a transgene/genomic junction region contained in the genome of ASR-368 and to a method for detection of the transgene/genomic junction region in bentgrass plant ASR-368 and progeny thereof.

SUMMARY OF THE INVENTION

The present invention is a bentgrass transgenic event designated ASR-368 having seed deposited with American Type Culture Collection (ATCC) with Accession No.PTA-4816. Another aspect of the invention is the progeny plants, or seeds, or regenerable parts of the plants and seeds of the bentgrass plant ASR-368. The invention also includes plant parts of bentgrass plant ASR-368 that include, but are not limited to pollen, ovule, flowers, shoots, roots, and leaves.

One aspect of the invention provides compositions and methods for detecting the presence of a transgene/genomic junction region from bentgrass plant event ASR-368. DNA molecules are provided that comprise at least one transgene/genomic junction DNA molecule selected from the group consisting of SEQ ID NO:1 and SEQ ID NO:2, and complements thereof, wherein the junction molecule spans the insertion site that comprises a heterologous DNA inserted into the bentgrass genome and the genomic DNA from the bentgrass cell flanking the insertion site in bentgrass event ASR-368. A bentgrass plant ASR-368 and seed comprising these molecules is an aspect of this invention.

A novel DNA molecule is provided that is a transgene/genomic region SEQ ID NO:3 or the complement thereof, wherein this DNA molecule is novel in bentgrass event ASR-368. A bentgrass plant and seed comprising SEQ ID NO:3 in the genome is an aspect of this invention.

According to another aspect of the invention, a DNA molecule is provided that is a transgene/genomic region SEQ ID NO:4, or the complement thereof, wherein this DNA molecule is novel in bentgrass event ASR-368. A bentgrass plant and seed comprising SEQ ID NO:4 in the genome is an aspect of this invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:3 and a DNA molecule of similar length of any portion of a 5' flanking bentgrass genomic DNA region of SEQ ID NO:3, wherein these DNA molecules when used together are useful as DNA primers in a DNA amplification method that produces an amplicon. The amplicon produced using these DNA primers in the DNA amplification method is diagnostic for bentgrass event ASR-368. Any amplicon comprising SEQ ID NO:1 produced by DNA primers homologous or complementary to any portion of SEQ ID NO:3 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO:4 and a DNA molecule of similar length of any portion of a 3' flanking bentgrass genomic DNA of SEQ ID NO:4, where these DNA molecules are useful as DNA primers in DNA amplification method. The amplicon produced using these DNA primers in the DNA amplification method is diagnostic for bentgrass event ASR-368. Any amplicon comprising SEQ ID NO:2 produced by DNA primers homologous or complementary to any portion of SEQ ID NO:4 is an aspect of the invention.

According to another aspect of the invention, methods of detecting the presence of DNA corresponding specifically to the bentgrass event ASR-368 DNA in a sample are provided. Such methods comprise: (a) contacting the sample comprising DNA with a primer set that, when used in a nucleic acid amplification reaction with genomic DNA from bentgrass event ASR-368 produces an amplicon that is diagnostic for bentgrass event ASR-368 (b) performing a nucleic acid amplification reaction, thereby producing the amplicon; and (c) detecting the amplicon.

According to another aspect of the invention, methods of detecting the presence of DNA corresponding specifically to the bentgrass event ASR-368 DNA in a sample are provided. Such methods comprising: (a) contacting the sample comprising DNA with a probe that hybridizes under stringent hybridization conditions with genomic DNA from bentgrass event ASR-368 and does not hybridize under the stringent hybridization conditions with a control bentgrass plant DNA; (b) subjecting the sample and probe to stringent hybridization conditions; and (c) detecting hybridization of the probe to the ASR-368 DNA.

According to another aspect of the invention, methods of producing a bentgrass plant that tolerates application of glyphosate are provided that comprise the steps of: (a) sexually crossing a first parental bentgrass event ASR-368 comprising the expression cassettes of the present invention, which confers tolerance to application of glyphosate, and a second parental bentgrass plant that lacks the glyphosate tolerance, thereby producing a plurality of progeny plants; and (b) selecting a progeny plant that tolerates application of glyphosate. Such methods may optionally comprise the further step of back-crossing the progeny plant to the second parental bentgrass plant and selecting for glyphosate tolerant progeny to produce a true-breeding bentgrass variety that tolerates application of glyphosate.

A turfgrass stand of grass that comprises bentgrass event ASR-368 is provided. The turfgrass stand of bentgrass ASR-368 that is glyphosate tolerant is especially useful on a golf course and these turfgrass stands are an aspect of the invention.

Another aspect of the invention is a method for controlling weeds in a turfgrass stand of bentgrass ASR-368 comprising the step of applying a glyphosate containing herbicide formulation to the turfgrass stand.

The foregoing and other aspects of the invention will become more apparent from the following detailed description and accompanying drawings.

BRIEF DESCRIPTION OF THE DRAWINGS

FIG. 3. ASR-368 5' transgene/genomic DNA sequence (SEQ ID NO:3)

FIG. 4. ASR-368 3' transgene/genomic DNA sequence (SEQ ID NO:4)

FIG. 5. ASR-368 5' transgene/genomic junction region (SEQ ID NO:1) and 3' transgene/genomic junction region (SEQ ID NO:2)

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR § 1.822 is used.

As used herein, the term "bentgrass" means *Agrostis stolonifera* and includes all plant varieties that can be bred with bentgrass ASR-368.

As used herein, the term "comprising" means "including but not limited to".

"Glyphosate" refers to N-phosphonomethylglycine and its salts, Glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation containing glyphosate. Examples of commercial formulations of glyphosate include, without restriction, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEO-FORCE, which contains glyphosate as its sodium salt; and that sold by Zeneca Limited as TOUCHDOWN® herbicide, which contains glyphosate as its trimethylsulfonium salt.

Figure 1:
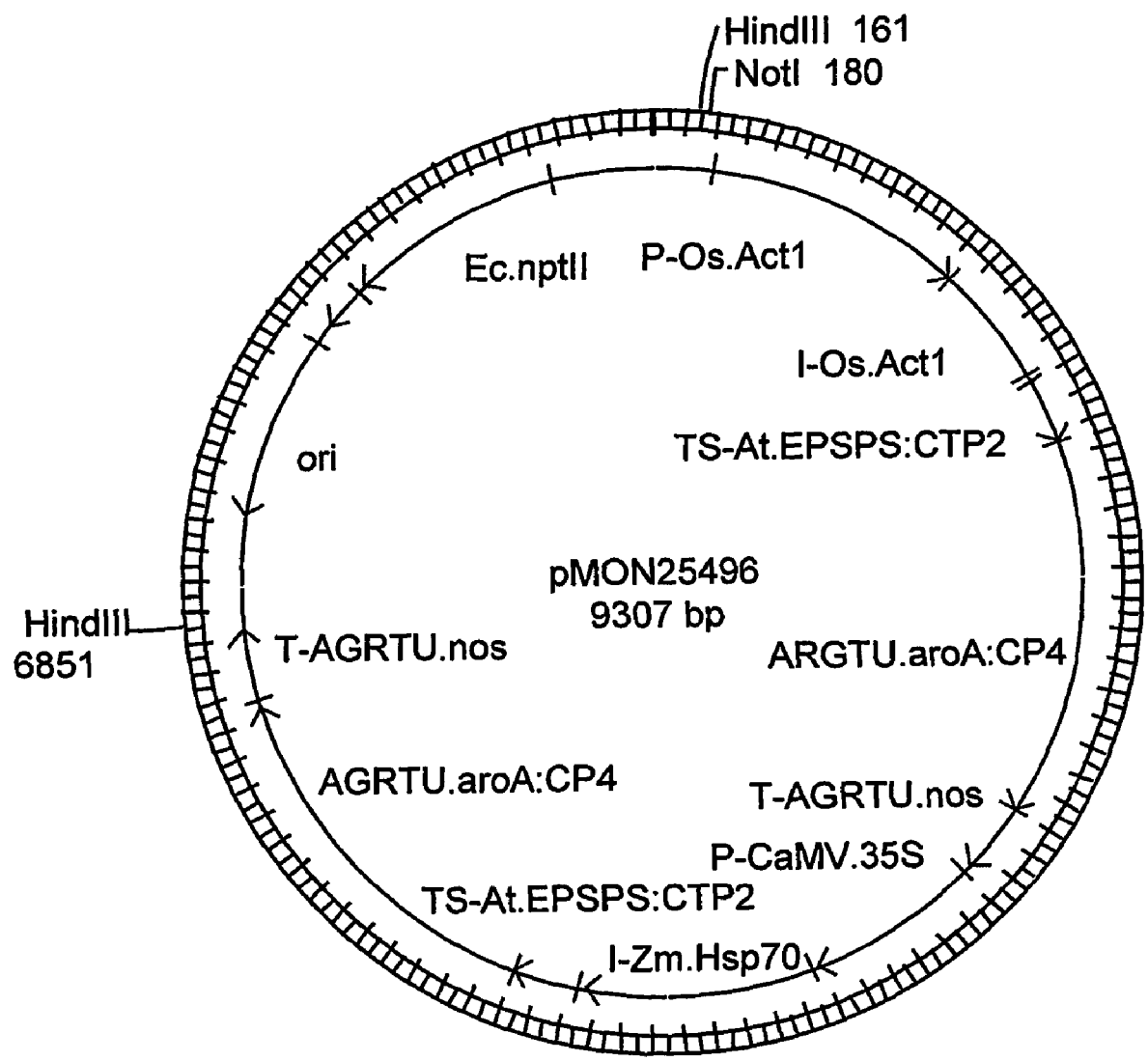
FIG. 1. Plasmid map of pMON25496

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another event that include the heterologous DNA. Even after repeated back-crossing to a recurrent parent, the inserted DNA and flanking genomic DNA from the transformed parent is present in the progeny of the cross at the same chromosomal location. The term "event" also refers to DNA from the original transformant comprising the inserted DNA and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA. A glyphosate tolerant bentgrass plant can be bred by first sexually crossing a first parental bentgrass plant consisting of a bentgrass plant grown from the transgenic bentgrass plant derived from transformation with the plant expression cassettes contained in pMON25496 (FIG. 1) that tolerates application of glyphosate herbicide, and a second parental bentgrass plant that lacks the tolerance to glyphosate herbicide, thereby producing a plurality of first progeny plants; and then selecting a first progeny plant that is tolerant to application of glyphosate herbicide; and selfing the first progeny plant, thereby producing a plurality of second progeny plants; and then selecting from the second progeny plants, a glyphosate herbicide tolerant plant. These steps can further include the back-crossing of the first glyphosate tolerant progeny plant or the second glyphosate tolerant progeny plant to the second parental bentgrass plant or a third parental bentgrass plant, thereby producing a bentgrass plant that tolerates the application of glyphosate herbicide. In the present invention, the transgenic bentgrass event is also defined as bentgrass event ASR-368 and may be referred to herein as ASR-368 or event ASR-368.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from bentgrass event ASR-368 whether from a bentgrass event ASR-368 plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic acid amplification methods.

Probes and primers are generally 11 polynucleotides or more in length, often 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules isolated from bentgrass ASR-368 the seed of which is deposited with the ATCC having accession number PTA-4816.

The nucleic acid probes and primers of the present invention hybridize under stringent conditions to a target DNA molecule. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO: 1, 2, 3, or 4, complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 through SEQ ID NO:4 or complements or fragments of either under high stringency conditions. In one aspect of the present invention, a preferred marker nucleic acid molecule of the present invention has the nucleic acid sequence set forth in SEQ ID NO:1 through SEQ ID NO:4 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:1 through SEQ ID NO:4 or complement thereof or fragments of either. In a further aspect of the present invention, a preferred marker nucleic acid molecule of the present invention shares between 95% and 100% sequence identity with the sequence set forth in SEQ ID NO:1 through SEQ ID NO:4 or complement thereof or fragments of either. SEQ ID NO:1 through SEQ IN NO:4 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification of a target polynucleic acid molecule that is part of a polynucleic acid template. For example, to determine whether a bentgrass plant resulting from a sexual cross contains transgenic event genomic DNA from the bentgrass event ASR-368 plant of the present invention, DNA that is extracted from a bentgrass plant tissue sample may be subjected to polynucleic acid amplification method using a primer pair that includes a primer derived from flanking DNA in the genome of the ASR-368 plant adjacent to the insertion site of the inserted heterologous DNA (transgenic DNA), and a second primer derived from the inserted heterologous DNA to produce an amplicon that is diagnostic for the presence of the ASR-368 event DNA. The amplicon is of a length and has a polynucleotide sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs or more. Alternatively, a primer pair can be derived from flanking genomic sequence on both sides of the inserted heterologous DNA so as to produce an amplicon that includes the entire insert polynucleotide sequence (e.g., a forward genomic primer from SEQ ID NO:3 and a reverse genomic primer from SEQ ID NO:4 that amplifies an inserted DNA molecule comprising the HindIII expression cassette of pMON25496 DNA fragment that was transformed into bentgrass, about 6681 nucleotide base pairs, FIG. 1). A member of a primer pair derived from the plant genomic sequence of ASR-368 may be located a distance from the inserted DNA molecule, this distance can range from one nucleotide base pair up to about twenty thousand nucleotide base pairs. The use of the term "amplicon" specifically excludes primer dimers that may be formed in the DNA thermal amplification reaction.

Polynucleic acid amplification can be accomplished by any of the various polynucleic acid amplification methods known in the art, including the polymerase chain reaction (PCR). A event of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA from bentgrass event ASR-368 can be verified (and corrected if necessary) by amplifying such DNA molecules from the event using primers derived from the sequences provided herein followed by standard DNA sequencing of the PCR amplicon or of the cloned DNA.

DNA detection kits that are based on DNA amplification methods contain DNA primers that specifically amplify a diagnostic amplicon. The kit may provide an agarose gel based detection method or any number of methods of detecting the amplicon known in the art.

The amplicon produced by these methods may be detected by a plurality of techniques. One such method is Genetic Bit Analysis (Nikiforov, et al. Nucleic Acid Res. 22:4167-4175, 1994), where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled dideoxynucleotide triphosphate (ddNTPs) specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. Deoxyribonucleotides (DNTPs) are added individually and the incorporation results in a light signal that is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

Bentgrass event ASR-368 is tolerant to glyphosate herbicide and is useful as a turfgrass stand. A turfgrass stand is cultivated in private and public areas. A good turfgrass stand, or green, has both beauty and usefulness; its maintenance for golf, tennis, baseball, football, and other sports fields is a costly and specialized procedure. The bentgrass ASR-368 event is especially useful as a turfgrass stand grown on golf courses. Golf courses have various turfgrass stand turfgrass components that make up a hole. These components include the tee, the fairway, the rough and the green. Event ASR-368 when used as a turfgrass provides a turfgrass stand that can be effectively managed for weed control by the application of a glyphosate containing herbicide. A turfgrass stand comprising the bentgrass event ASR-368 is an aspect of the invention, whereas the ASR-368 turfgrass stand is a component of a golf course, then that component is an aspect of the invention. A turfgrass stand of the present invention preferably comprises bentgrass event ASR-368 as a 50 percent or more component, more preferably a 75 percent component, and even more preferably greater than a 90 percent component.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Figure 2:
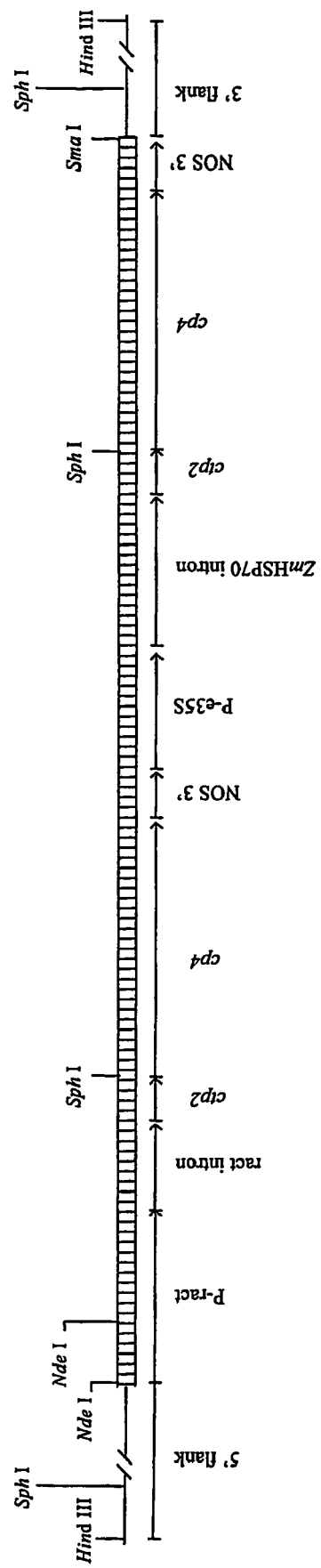
FIG. 2. Genomic organization of insert in Bentgrass event ASR-368

The transgenic bentgrass event ASR-368 was generated by microprojectile bombardment of bentgrass line B99061R/990028 using a linear HindIII DNA fragment derived from pMON25496 (FIG. 1) that comprises the transgene insert of the present invention. This DNA fragment contains two transgene expression cassettes that collectively confer bentgrass ASR-368 plant tolerance to glyphosate. The first cassette is composed of the rice actin 1 promoter and intron (P-Os.Act1, also referred to as P-ract, and the intron I-Os.Act1, also referred to as ract intron, U.S. Pat. No. 5,641,876), operably connected to an *Arabidopsis* EPSPS chloroplast transit peptide (TS-At.EPSPS:CTP2, also referred to as ctp2, Klee et al., Mol. Gen. Genet. 210:47-442, 1987), operably connected to a glyphosate tolerant 5-enol-pyruvylshikimate-3-phosphate synthase (EPSPS) from *Agrobacterium* sp. strain CP4 (AGR- TU.aroA:CP4 EPSPS, also known as cp4, U.S. Pat. No. 5,633,435) and operably connected to a nopaline synthase transcriptional terminator (T-nos, also referred to as NOS 3', Fraley et al. Proc. Natl. Acad. Sci. USA 80:4803-4807, 1983). The second transgene expression cassette consists of the cauliflower mosaic virus 35S promoter containing a tandem duplication of the enhancer region (P-CaMV.35S, also referred to as P-e35S, Kay et al. Science 236:1299-1302, 1987; U.S. Pat. No. 5,164,316), operably connected to a *Zea mays* Hsp70 intron (I-Zm.Hsp70, also referred to as ZmHSP70 intron, U.S. Pat. No. 5,362,865), operably connected to an *Arabidopsis* EPSPS chloroplast transit peptide (TS-At.EPSPS:CTP2), operably connected to a glyphosate tolerant 5-enol-pyruvylshikimate-3-phosphate synthase (EPSPS) from *Agrobacterium* sp. strain CP4 (AGRTU.aroA: CP4 EPSPS) and operably connected to a nopaline synthase transcriptional terminator (T-nos, Fraley et al. Proc. Natl. Acad. Sci. USA 80:4803-4807, 1983). The DNA construct pMON25496 has been shown to confer glyphosate tolerance in transgenic corn (US 20020013960 A1). Post-bombardment, glyphosate-tolerant transgenic calli were selected on media containing 3 mM glyphosate and plants were subsequently regenerated. Transgenic events were produced and event ASR-368 was selected from this population based on a superior combination of characteristics, including glyphosate tolerance, agronomic performance, and single transgenic insertion. The transgene insertion as it occurs in ASR-368 is shown in FIG. 2.

Example 2

The glyphosate tolerant bentgrass event ASR-368 was tested for tolerance to glyphosate vegetative injury. The glyphosate tolerant bentgrass event ASR-368 showed no damage to 5% Roundup® Pro (glyphosate containing herbicide formulation) sprayed with a hand sprayer or an amount equivalent to 128 ounces Roundup® Pro per acre. The standard recommended rate is 1.25 to 2.5% Roundup® Pro or amount equivalent to 32 to 64 ounces Roundup® Pro per acre. Three applications of the glyphosate containing herbicide formulation during the growing season, early summary, mid-summer and early fall were used to test for glyphosate tolerance in a turfgrass stand of event ASR-368. Bentgrass event ASR-368 showed glyphosate tolerance to all applications of glyphosate at three test locations. No vegetative injury was observed on event ASR-368, while bentgrass plants not containing pMON25496 were all heavily injured or killed by the glyphosate containing herbicide formulation treatment. Treatment of bentgrass ASR-368 that is a turfgrass component of a turfgrass stand with a glyphosate containing herbicide is a method useful for controlling weeds and other unwanted plants in the turfgrass stand.

Example 3

The DNA sequences of the 5' and 3' genomic regions adjacent to the transgene insert are determined by isolation of the DNA molecules using Clontech's Universal Genome Walker™ Kit and the RAGE method (Rapid Amplification of Genomic DNA Ends). The 5' transgene/genomic DNA (FIG. 3) is isolated from bentgrass ASR-368 genomic DNA by: digestion overnight at 37° C. with HindIII, and digestion of pBluescript KS plasmid (Stratagene, La Jolla Calif.) for 3 hours at 37° C. with XbaI. The four nucleotide base overhangs are filled in with two nucleotides to become compatible for ligation. The genomic DNA is ligated with the XbaI digested/2 nucleotide base filled pBluescript KS plasmid by incubation with T4 DNA ligase under the appropriate conditions. After ligation reaction, 5 μl of the ligation mix is used in a DNA amplification method with 2 μl of 10 μM M13 forward primer (SEQ ID NO:5), 2 μl 10 μM ASR-368 transgene-specific oligonucleotide primer (SEQ ID NO:6), 1.75 μl 10 mM deoxyribonucleotides, the Expand Long Template PCR System (Roche) and water to 50 μl. A primary reaction is performed in a thermocycler with the following cycling conditions: 30 cycles of 94 C for 2 minutes; 94 C for 10 seconds each; 56 C for 30 seconds, 68 C for 3 minutes; and finally 68 C for 10 minutes. One μl of the primary reaction is amplified in a secondary reaction that includes 2 μl of 10 μM T7 primer (SEQ ID NO:7), 2 μl of ASR-368 specific primer (SEQ ID NO:8), 1.75 μl 10 mM deoxyribonucleotides, the Expand Long Template PCR System (Roche) and water to 50 μl, the thermocycler conditions are the same as used for the primary reaction.

The presence of the transgene/genomic DNA in a bentgrass sample is verified by PCR. The 5' transgene/genomic junction region amplicon is produced using one primer (SEQ ID NO:11), designed to the genomic DNA sequence flanking the 5' end of the insert paired with a second primer (SEQ ID NO:12) in the rice actin 1 promoter of the inserted transgene DNA. The 5' junction amplicon is produced from about 50 ng of leaf genomic DNA (1 μl) as a template, 15 pmol of each primer (1.5 μl each), and the Expand High Fidelity PCR system in a 50 μl reaction volume. The amplification of the reactions was performed under the following cycling conditions: 1 cycle at 94° C. for 2 minutes; 10 cycles at 94° C. for 15 seconds, 60° C. for 30 seconds, 72° C. for 1 minute; 25 cycles at 94° C. for 15 seconds, 60° C. for 30 seconds 72° C. for 1 minute+5 additional seconds per cycle; 1 cycle 72° C. for 7 minutes.

In another method, the isolation of the corresponding transgene/genomic DNA molecules from bentgrass event ASR-368 can also be accomplished using ligated adapters and nested PCR as described in the Genome Walker™ kit (catalog #K1807-1, CloneTech Laboratories, Inc, Palo Alto, Calif.). First, genomic DNA from the ASR-368 event is isolated by the CTAB purification method (Rogers et al., Plant Mol. Biol. 5:69-76, 1985). The genomic DNA libraries for amplification are prepared according to manufacturer's instructions (Genome Walker™, CloneTech Laboratories, Inc, Palo Alto, Calif.). In separate reactions, genomic DNA is digested overnight at 37° C. with blunt-end restriction endonucleases (CloneTech Laboratories, Inc, Palo Alto, Calif.). The reaction mixtures are extracted with phenol:chloroform, the DNA is precipitated by the addition of ethanol to the aqueous phase, pelleted by centrifugation, then resuspended in Tris-EDTA buffer (10 mM Tris-.HCl, pH 8.0, 1 mM EDTA). The purified blunt-ended genomic DNA fragments are ligated to the Genome Walker™ adapters according to the manufacturer's protocol. After ligation, each reaction is heat treated (70° C. for 5 min) to terminate the reaction and then diluted 10-fold in Tris-EDTA buffer. One μl of each respective ligation is then amplified in a 50 μl reaction that included 1 μl of respective adapter-ligated library, 1 μl of 10 μM Genome Walker™ adapter primer AP1 (SEQ ID NO:9, supplied by manufacturer), 1 μl of 10 μM event ASR-368 transgene-specific oligonucleotide (SEQ ID NO:12), 1 μl 10 mM deoxyribonucleotides, 2.5 μl dimethyl sulfoxide, 5 μl of 10× PCR buffer containing $MgCl_2$, 0.5 μl (2.5 units) of Amplitaq thermostable DNA polymerase (PE Applied Biosystems, Foster City, Calif.), and $H_2O$ to 50 μl. The reactions are performed in a thermocycler using calculated temperature control and the following cycling conditions: 1 cycle of 95° C. for 9 minutes; 7 cycles of 94° C. for 2 seconds, 70° C. for 3 minutes; 36 cycles of 94° C. for 2 seconds, 65° C. for 3 minutes; 1 cycle of 65° C. for 4 minutes. One μl of each primary reaction is diluted 50-fold with water and amplified in a secondary reaction (1 μl of respective diluted primary reaction, 1 μl of 10 μM Genome Walker™ nested adapter primer AP2, (SEQ ID NO: 10, supplied by manufacturer), 1 μl of 10 μM event ASR-368 transgene-specific nested oligonucleotide (SEQ ID NO:12), 1 μl 10 mM deoxyribonucleotides, 2.5 μl dimethyl sulfoxide, 5 μl of 10×PCR buffer containing MgCl₂, 0.5 μl (2.5 units) of Amplitaq thermostable DNA polymerase (PE Applied Biosystems, Foster City, Calif.), and H₂O to 50 μl) using the following cycling conditions: 1 cycle of 95° C. for 9 minutes; 5 cycles of 94° C. for 2 seconds, 70° C. for 3 minutes; 24 cycles of 94° C. for 2 seconds, 65° C. for 3 minutes; 1 cycle of 65° C. for 4 minutes.

PCR products, representing 5' regions that span the junction between the bentgrass event ASR-368 transgenic insertion and the neighboring flanking bentgrass genomic DNA sequence are purified by agarose gel electrophoresis followed by isolation from the agarose matrix using the QIAquick Gel Extraction Kit (catalog #28704, Qiagen Inc., Valencia, Calif.) and direct cloning into the pGEM-T Easy vector (catalog. #A1360, Promega, Madison, +Wis.). The identity of the cloned PCR products and relationship to the HindIII fragment of pMON25496 that was used to produce bentgrass ASR-368 is confirmed by DNA sequence analysis (ABI Prism™ 377, PE Biosystems, Foster City, Calif. and DNASTAR sequence analysis software, DNASTAR Inc., Madison, Wis.). The DNA sequence of the 5' genomic/transgene region DNA molecule is illustrated in FIG. 3. FIG. 3 further identifies the bentgrass genomic DNA portion by showing it as underlined DNA sequence, the double underlined DNA sequence is DNA sequence homologous or complementary to PCR primer molecules useful in the identification of a bentgrass genome that contains SEQ ID NO:3.

Similarly, the bentgrass event ASR-368 3' flanking genomic DNA sequence (FIG. 4) is amplified using one primer (SEQ ID NO:14) designed to the genomic DNA sequence flanking the 3' end of the transgene insert and a second primer (SEQ ID NO:13) located in the T-nos 3' transcription termination region contained in pMON25496. The PCR is conducted using about 211 ng of leaf genomic DNA (1 μl) as a template, 15 pmol of each primer (1.5 μl each), and the Expand Long Template PCR system (Roche) in a 50 μl reaction volume. The amplification of the reactions is performed under the following cycling conditions: 1 cycle at 94° C. for 2 minutes; 35 cycles at 94° C. for 10 seconds, 60° C. for 30 seconds, 68° C. for 30 seconds; 1 cycle at 68° C. for 10 minutes.

Bentgrass genomic DNA sequence flanking both sides of the transgenic insertion was determined for event ASR-368 by sequencing the Genome Walker™-derived amplification products and alignment to known transgene sequence. A 5' region of the transgene insertion site was sequenced, this region comprises a transgene/genomic DNA sequence of 896 nucleotide base pairs (bps) (SEQ ID NO:3) around the insertion junction. This DNA sequence consists of 637 bps of the flanking bentgrass genomic sequence (nucleotides 1-637 of SEQ ID NO:3), and 259 bps of sequence from the 5' end of P-Os.Actl (nucleotides 638-896 of SEQ ID NO:3) as shown in FIG. 3.

The DNA sequence was determined for a 474 bps segment (SEQ ID NO:4) around the 3' insertion junction, which from the 5' end of the segment has 248 bps of the T-nos transcriptional terminator (nucleotides 1-248 of SEQ ID NO:4), and the remaining sequence consisting of bentgrass genomic DNA sequence flanking the integration site (corresponding to bases 249-474 of SEQ ID NO:4) as shown in FIG. 4. The double underlined DNA sequence is DNA sequence homologous or complementary to PCR primer molecules useful in the identification of a bentgrass genome that contains SEQ ID NO:4

The junction sequences, SEQ ID NO:1 and SEQ ID NO:2 (FIG. 5) are novel DNA sequences from event ASR-368 and are diagnostic for bentgrass plant event ASR-368 and its progeny. The junction sequences in SEQ ID NO:1 and SEQ ID NO:2 comprise polynucleotides on each side of an insertion site of a transgene sequence fragment and bentgrass genomic DNA. The junction sequence SEQ ID NO:1 is found at nucleotide position 626-649 of SEQ ID NO:3, the 5' region of the transgene insertion site. The junction sequence SEQ ID NO:2 is located at nucleotide position 236-259 of SEQ ID NO:4, the 3' region of the transgene insertion site. Either junction sequence can be used as a DNA probe or primer to specifically identify genomic DNA of event ASR-368.

Example 4

DNA event primer pairs are used to produce an amplicon diagnostic for bentgrass event ASR-368. Amplicons diagnostic for ASR-368 comprise at least one junction sequence, SEQ ID NO:1 or SEQ ID NO:2. ASR-368 event primer pairs that will produce a diagnostic amplicon for bentgrass ASR-368 include, but are not limited to a primer pair that includes event primer 1 (SEQ ID NO:11) and event primer 2 (SEQ ID NO:12) that provide a 5' amplicon DNA molecule, and a primer pair, SEQ ID NO:13 and SEQ ID NO:14 that when substituted for primers 1 and 2 in the protocol outlined in Table 1 produce the 3' amplicon DNA molecule. In addition to these primer pairs, any primer pair derived from SEQ ID NO:3 or SEQ ID NO:4 that in a DNA amplification reaction produces an amplicon diagnostic for bentgrass event ASR-368 is an aspect of the present invention. Any single isolated DNA polynucleotide primer molecule comprising at least 11 contiguous nucleotides of SEQ ID NO:3, or its complement that is useful in a DNA amplification method to produce an amplicon diagnostic for bentgrass event ASR-368 is an aspect of the invention. Any single isolated DNA polynucleotide primer molecule comprising at least 11 contiguous nucleotides of SEQ ID NO:4, or its complement that is useful in a DNA amplification method to produce an amplicon diagnostic for bentgrass event ASR-368 is an aspect of the invention. The amplification conditions for this analysis are illustrated in Table 1 and Table 2, however, any modification of these methods that use DNA primers to produce an amplicon diagnostic for bentgrass event ASR-368 is within the ordinary skill of the art. A diagnostic amplicon comprises at least one transgene/genomic junction DNA (SEQ ID NO:1 or SEQ ID NO:2).

An analysis for event ASR-368 plant tissue sample should include a positive tissue control from event ASR-368, a negative control from a bentgrass plant that is not event ASR-368, and a negative control that contains no bentgrass DNA. Additional primer sequences can be selected from SEQ ID NO:3 and SEQ ID NO:4 by those skilled in the art of DNA amplification methods, and conditions selected for the production of an amplicon may the methods shown in Table 1 and Table 2 or differ, but result in an amplicon diagnostic for event ASR-368. The use of these DNA primer sequences with modifications to the methods of Table 1 and 2 are within the scope of the invention. The amplicon produced by at least one DNA primer sequence derived from SEQ ID NO:3 or SEQ ID NO:4 that is diagnostic for ASR-368 is an aspect of the invention.

DNA detection kits that contain at least one DNA primer derived from SEQ ID NO:3 or SEQ ID NO:4 that when used in a DNA amplification method produces a diagnostic amplicon for bentgrass ASR-368 is an aspect of the invention. The amplicon produced by at least one primer sequence derived from any of the genetic elements of pMON25496 that is diagnostic for ASR-368 is an aspect of the invention. A bentgrass plant or seed, wherein its genome will produce an amplicon diagnostic for bentgrass event ASR-368 when tested in a DNA amplification method to amplify a DNA molecule from DNA extracted from said bentgrass plant or seed is an aspect of the invention. The assay for the ASR-368 amplicon can be performed by using a Stratagene Robocycler, MJ Engine, Perkin-Elmer 9700, or Eppendorf Mastercycler Gradient thermocycler as shown in Table 2, or by methods and apparatus known to those skilled in the art.

TABLE 1

PCR procedure and reaction mixture conditions for the identification of bentgrass event ASR-368 5' transgene insert/genomic junction region.

| Step | Reagent | Amount | Comments |
|---|---|---|---|
| 1 | Nuclease-free water | add to final volume of 20 μl | — |
| 2 | 10X reaction buffer (with MgCl$_2$) | 2.0 μl | 1X final concentration of buffer, 1.5 mM final concentration of MgCl$_2$ |
| 3 | 10 mM solution of dATP, dCTP, dGTP, and dTTP | 0.4 μl | 200 μM final concentration of each dNTP |
| 4 | event primer 1 (SEQ ID NO:11) (resuspended in 1X TE buffer or nuclease-free water to a concentration of 10 μM) | 0.4 μl | 0.2 μM final concentration |
| 5 | event primer 2 (SEQ ID NO:12) (resuspended in 1X TE buffer or nuclease-free water to a concentration of 10 μM) | 0.4 μl | 0.2 μM final concentration |
| 6 | RNase, DNase free (500 ng/μl) | 0.1 μl | 50 ng/reaction |
| 7 | REDTaq DNA polymerase (1 unit/μl) | 1.0 μl (recommended to switch pipets prior to next step) | 1 unit/reaction |
| 8 | Extracted DNA (template): Samples to be analyzed | | — |
|  | individual leaves | 10-200 ng of genomic DNA | |
|  | pooled leaves (maximum of 50 leaves/pool) | 200 ng of genomic DNA | |
|  | Negative control | 50 ng of bentgrass genomic DNA (not ASR-368) | |
|  | Negative control | no template DNA | |
|  | Positive control | 50 ng of ASR-368 genomic DNA | |

TABLE 2

Suggested PCR parameters for different thermocyclers
Gently mix and, if needed (no hot top on thermocycler), add 1-2 drops of mineral oil on top of each reaction. Proceed with the PCR in a Stratagene Robocycler, MJ Engine, Perkin-Elmer 9700, or Eppendorf Mastercycler Gradient thermocycler using the following cycling parameters.

| Cycle No. | Settings: Stratagene Robocycler | |
|---|---|---|
| 1 | 94° C. | 3 minutes |
| 38 | 94° C. | 1 minute |
|  | 60° C. | 1 minute |
|  | 72° C. | 1 minute and 30 seconds |
| 1 | 72° C. | 10 minutes |

| Cycle No. | Settings: MJ Engine or Perkin-Elmer 9700 | |
|---|---|---|
| 1 | 94° C. | 3 minutes |
| 38 | 94° C. | 10 seconds |
|  | 60° C. | 30 seconds |
|  | 72° C. | 1 minute |
| 1 | 72° C. | 10 minutes |

Note:
The MJ Engine or Eppendorf Mastercycler Gradient thermocycler should be run in the calculated mode. Run the Perkin-Elmer 9700 thermocycler with the ramp speed set at maximum.

A deposit of the Monsanto Company, bentgrass seed ASR-368 disclosed above and recited in the claims gas been made under the Budapest Treaty with the American Type Culture Collection (ATCC), 10801 University Boulevard, Manassas, Va. 20110. The ATCC accession number is PTA-4816. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

The invention claimed is:

1. A seed of bentgrass plant designated ASR-368, having representative seed of said bentgrass plant having been deposited under ATCC Accession No. PTA-4816.

2. A bentgrass plant ASR-368 or part thereof produced by growing the seed of claim 1.

3. The bentgrass plant ASR-368 or part thereof of claim 2, comprising pollen, ovule, seed, roots, or leaves.

4. A progeny seed of the bentgrass plant ASR-368 of claim 2 wherein said progeny seed comprises a DNA molecule selected from the group consisting of SEQ ID NO:1, SEQ ID NO:2, SEQ ID NO:3, and SEQ ID NO:4.

5. A bentgrass plant grown from said progeny seed of claim 4, wherein the genome of said bentgrass plant comprises a DNA molecule selected from the group consisting of SEQ ID NO:1, SEQ ID NO:2, SEQ ID NO:3, and SEQ ID NO:4.

6. A method of producing a plant that tolerates application of glyphosate herbicide comprising:
   (a) sexually crossing a first glyphosate tolerant bentgrass plant ASR-368 having representative seed of said bentgrass plant deposited under ATCC Accession No. PTA-4816 and a second parent bentgrass plant that lacks the tolerance to glyphosate herbicide, thereby producing a plurality of progeny plants; and
   (b) selecting a progeny plant that is tolerant to application of glyphosate.

7. The method of claim 6 further comprising the step of backcrossing the first progeny plant that is glyphosate tolerant or the second progeny plant that is glyphosate tolerant to the second parent plant or a third parent plant, thereby producing a plant that tolerates the application of glyphosate.

8. A bentgrass plant, seed, or DNA-containing part thereof comprising bentgrass event ASR-368.

9. A bentgrass plant, seed, or DNA-containing part thereof capable of producing an ASR-368 diagnostic amplicon.

10. The bentgrass plant, seed, or DNA-containing part thereof of claim 9, wherein the ASR-368 diagnostic amplicon comprises SEQ ID NO:1 or SEQ ID NO:2.

* * * * *

UNITED STATES PATENT AND TRADEMARK OFFICE
CERTIFICATE OF CORRECTION

PATENT NO. : 7,569,747 B2  Page 1 of 1
APPLICATION NO. : 10/537393
DATED : August 4, 2009
INVENTOR(S) : Guo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 461 days.

Signed and Sealed this

Seventh Day of September, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: chimeric DNA of bentgrass genomic DNA and
      transgene insert DNA
```

```
<220> FEATURE:
<221> NAME/KEY: misc_feature
<222> LOCATION: (1)..(24)
<223> OTHER INFORMATION: 5' transgene/genomic junction DNA, a chimeric
      DNA of bentgrass genomic DNA and transgene insert DNA

<400> SEQUENCE: 1
gacatatgct taagaagaga gtcg                                                24

<210> SEQ ID NO 2
<211> LENGTH: 24
<212> TYPE: DNA
<213> ORGANISM: Artificial Sequence
<220> FEATURE:
<223> OTHER INFORMATION: chimeric DNA of bentgrass genomic DNA and
      transgene insert DNA
<220> FEATURE:
<221> NAME/KEY: misc_feature
<222> LOCATION: (1)..(24)
<223> OTHER INFORMATION: 3' transgene/genomic DNA junction, a chimeric
      DNA of bentgrass genomic DNA and transgene insert DNA

<400> SEQUENCE: 2
aattcggtac catgtaccac gaac                                                24

<210> SEQ ID NO 3
<211> LENGTH: 896
<212> TYPE: DNA
<213> ORGANISM: Artificial Sequence
<220> FEATURE:
<223> OTHER INFORMATION: chimeric DNA of bentgrass genomic DNA and
      transgene insert DNA
<220> FEATURE:
<221> NAME/KEY: misc_feature
<222> LOCATION: (1)..(896)
<223> OTHER INFORMATION: 5' transgene/genomic region, a chimeric DNA of
      bentgrass genomic DNA and transgene insert DNA

<400> SEQUENCE: 3
aagcgagtat cctgataaga aggaagaag acgatcgctc tgtctatggg cggggctcag          60
ggcgacgaca gaaccagagc tttcgtcgtg aacaaaacag ggaaggacca aagcaggaga        120
agaggagagg aaacagagag aaagagggg ttggtaggta cttggtggtc cctgctactt         180
ctccaacagc agcagaaagg aaagaagaac gaaccaaggc acaagtacgc tccaaccgag        240
ccatcccttt cttcccttta tcattgactt taatcatgag aaatctaatt aattaattaa        300
actctacgca aaaggcatat aaaattgtca attatgcaag gcagttgccc tgtttctggt        360
agccggttac aacacaggaa gacaaccaaa agcgtcggaa aagtgagttt agtcgaatct        420
gaattcaatg tgaaagattt ttgtaaagaa tgaaataaat cccgataaaa aagaatgaa         480 caaaaggaaa ctaaaaaact gtggatgtga gtccaacgtt taagcatatc gatgcaaacg        540
tgatgaagaa ccaaacgcgc cggcggaaga cggattcccg gaagaccaaa ttaaagacga        600
tagttgtcga gcaaacgacc aaaagaagaa gatccgacat atgcttaaga agagagtcgg       660
gatagtccaa aataaaacaa aggtaagatt acctggtcaa agtgaaaac atcagttaaa        720 aggtggtata agtaaaaata tcggtaataa aaggtggccc aaagtgaaat ttactctttt       780
ctactattat aaaaattgag gatgttttg tcggtacttt gatacgtcat ttttgtatga        840
attggttttt aagtttattc gcttttggaa atgcatatct gtatttgagt cgggtt            896

<210> SEQ ID NO 4
<211> LENGTH: 474
<212> TYPE: DNA
<213> ORGANISM: Artificial Sequence
```

```
<220> FEATURE:
<223> OTHER INFORMATION: chimeric DNA of bentgrass genomic DNA and
      transgene insert DNA

<400> SEQUENCE: 4
agattgaatc ctgttgccgg tcttgcgatg attatcatat aatttctgtt gaattacgtt    60
aagcatgtaa taattaacat gtaatgcatg acgttattta tgagatgggt ttttatgatt   120
agagtcccgc aattatacat ttaatacgcg atagaaaaca aaatatagcg cgcaaactag   180
gataaattat cgcgcgcggt gtcatctatg ttactagatc ggggatatcc ccggggaatt   240
cggtaccatg taccacggaa cagaaaaaag aaaggcccac ggttgtgcag gaaacggcca   300
ccgcgcgagc cagcgcctca cgcctcatcc gccattccgt cgagcacccc gcacgcgccg   360
ccgctgctat gctcctccgg ccgcgcccct tcctcctcca ggtcctcacg ccgcttcgct   420
cctcccgcgc cccctcgcg gtccgccgca cgctctcagc gcacgccgcg gcag          474

<210> SEQ ID NO 5
<211> LENGTH: 23
<212> TYPE: DNA
<213> ORGANISM: bacteriophage M13

<400> SEQUENCE: 5
cgccagggtt ttcccagtca cga                                            23

<210> SEQ ID NO 6
<211> LENGTH: 30
<212> TYPE: DNA
<213> ORGANISM: Artificial Sequence
<220> FEATURE:
<223> OTHER INFORMATION: synthetic DNA primer molecule

<400> SEQUENCE: 6
tgacgtatca aagtaccgac aaaaacatcc                                     30

<210> SEQ ID NO 7
<211> LENGTH: 23
<212> TYPE: DNA
<213> ORGANISM: bacteriophage T7

<400> SEQUENCE: 7
taatacgact cactataggg cga                                            23

<210> SEQ ID NO 8
<211> LENGTH: 30
<212> TYPE: DNA
<213> ORGANISM: Agrostis stolonifera
<220> FEATURE:
<221> NAME/KEY: misc_feature
<222> LOCATION: (1)..(30)
<223> OTHER INFORMATION: ASR-368 genomic DNA primer molecule

<400> SEQUENCE: 8
cctttgtttt attttggact atcccgactc                                     30

<210> SEQ ID NO 9
<211> LENGTH: 26
<212> TYPE: DNA
<213> ORGANISM: Artificial Sequence
<220> FEATURE:
<223> OTHER INFORMATION: synthetic primer molecule AP1
```

-continued

```
<220> FEATURE:
<221> NAME/KEY: misc_feature
<222> LOCATION: (1)..(26)
<223> OTHER INFORMATION: artificial primer molecule AP1 from Genome
      Walker

<400> SEQUENCE: 9
agattgaatc ctgttgccgg tcttgc                                              26

<210> SEQ ID NO 10
<211> LENGTH: 28
<212> TYPE: DNA
<213> ORGANISM: Artificial Sequence
<220> FEATURE:
<223> OTHER INFORMATION: synthetic primer molecule AP2
<220> FEATURE:
<221> NAME/KEY: misc_feature
<222> LOCATION: (1)..(28)
<223> OTHER INFORMATION: artificial primer molecule AP2 from Genome
      Walker

<400> SEQUENCE: 10
gcggtgtcat ctatgttact agatcggg                                            28

<210> SEQ ID NO 11
<211> LENGTH: 29
<212> TYPE: DNA
<213> ORGANISM: Agrostis stolonifera

<400> SEQUENCE: 11
aagcgagtat cctgataaga aaggaagaa                                           29

<210> SEQ ID NO 12
<211> LENGTH: 30
<212> TYPE: DNA
<213> ORGANISM: Oryza sativa

<400> SEQUENCE: 12
aacccgactc aaatacagat atgcatttcc                                          30

<210> SEQ ID NO 13
<211> LENGTH: 25
<212> TYPE: DNA
<213> ORGANISM: Agrobacterium tumefaciens

<400> SEQUENCE: 13
agattgaatc ctgttgcggt cttgc                                               25

<210> SEQ ID NO 14
<211> LENGTH: 21
<212> TYPE: DNA
<213> ORGANISM: Agrostis stolonifera

<400> SEQUENCE: 14
ctgccgcggc gtgcgctgag a                                                   21
```